(12) United States Patent
Uchida et al.

(10) Patent No.: US 8,080,704 B2
(45) Date of Patent: Dec. 20, 2011

(54) ABSORBENT ARTICLE

(75) Inventors: Kensaku Uchida, Tokyo (JP); Ikuo Kubota, Tokyo (JP); Hideyuki Ishiguro, Tokyo (JP); Nobuyuki Kamishioiri, Tochigi (JP)

(73) Assignee: Kao Corporation, Tokyo (JP)

( * ) Notice: Subject to any disclaimer, the term of this patent is extended or adjusted under 35 U.S.C. 154(b) by 118 days.

(21) Appl. No.: 12/443,389

(22) PCT Filed: Sep. 26, 2007

(86) PCT No.: PCT/JP2007/068650
§ 371 (c)(1),
(2), (4) Date: May 5, 2009

(87) PCT Pub. No.: WO2008/038654
PCT Pub. Date: Apr. 3, 2008

(65) Prior Publication Data
US 2009/0326494 A1   Dec. 31, 2009

(30) Foreign Application Priority Data

Sep. 29, 2006 (JP) ................................. 2006-266149
Jun. 25, 2007 (JP) ................................. 2007-166618

(51) Int. Cl.
*A61F 13/15* (2006.01)
(52) U.S. Cl. ......... 604/361; 604/365; 604/367; 604/362
(58) Field of Classification Search ................. 604/361, 604/365, 367, 362
See application file for complete search history.

(56) References Cited

U.S. PATENT DOCUMENTS

| 4,681,576 A | 7/1987 | Colon et al. | |
| 4,743,238 A * | 5/1988 | Colon et al. | 604/361 |
| 5,413,568 A * | 5/1995 | Roach et al. | 604/358 |
| 6,904,865 B2 * | 6/2005 | Klofta et al. | 116/206 |

FOREIGN PATENT DOCUMENTS

| JP | 2-58585 A | 2/1990 |
| JP | 3-221039 A | 9/1991 |
| JP | 2004-512425 A | 4/2004 |
| JP | 2004-352334 A | 12/2004 |
| JP | 2005-261466 A | 9/2005 |
| WO | WO-02/36177 A2 | 5/2002 |
| WO | WO-2006/073096 A1 | 7/2006 |

OTHER PUBLICATIONS

International Preliminary Report on Patentability and Written Opinion of the International Searching Authority (Forms PCT/IB/338, PCT/IB/373 and PCT/ISA/237) for International Application No. PCT/JP2007/068650 filed on Sep. 26, 2007.

* cited by examiner

*Primary Examiner* — Jacqueline F. Stephens
(74) *Attorney, Agent, or Firm* — Birch, Stewart, Kolasch & Birch, LLP

(57) ABSTRACT

A wetness indicator composition contains (a) 0.1% to 5% by weight of a pH indicator that is substantially colorless at pH 7 and develops a color in an acidic environment, (b) 20% to 90% by weight of a surfactant, (c) 5% to 55% by weight of a polyalkylene glycol, (d) 0% to 70% by weight of a polymer having a carboxyl group, and (e) 0.1% to 5% by weight of an acidic substance other than components (b) and (d). In an absorbent article including a topsheet 2, a backsheet 3, and an absorbent member 4 interposed between the topsheet 2 and the backsheet 3 and having applied thereon a hot-melt composition that changes color on contact with a body fluid, the wetness indicator composition is used as the hot melt composition.

4 Claims, 4 Drawing Sheets

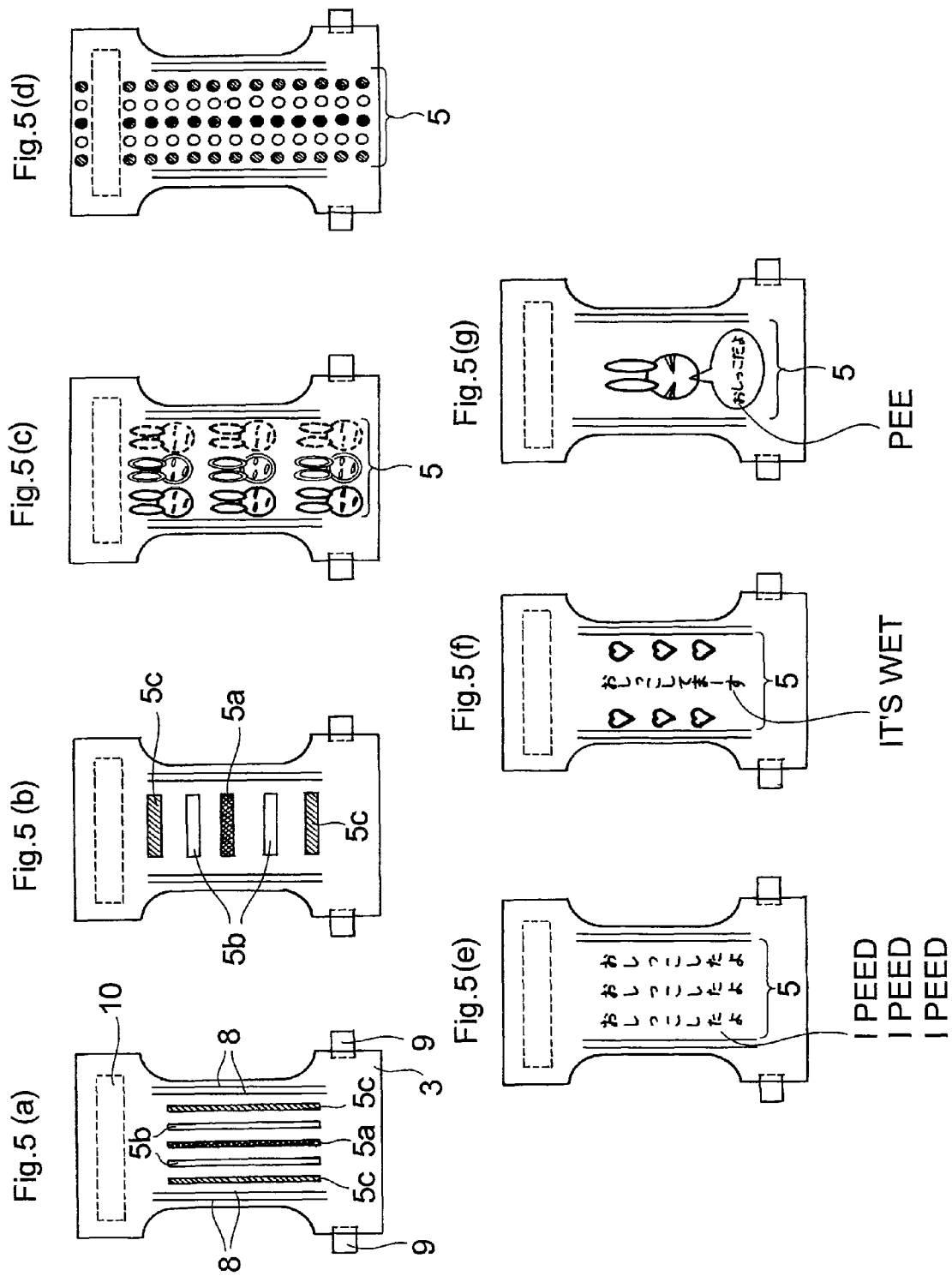

ABSORBENT ARTICLE

TECHNICAL FIELD

The present invention relates to an absorbent article having a wetness indicator composition. The wetness indicator composition used in the invention has thermoplasticity and flexibility, is initially colorless in hue, and develops a color in rapid response to being wetted with water to indicate wetness. Such characteristics being best taken advantage of, the wetness indicator is effective in various applications.

BACKGROUND ART

A wetness indicator has recently been used as a device that signals wetness with water. Among known uses of a wetness indicator is application to a disposable, nonwoven fabric absorbent article for infants such that a caregiver may know whether a diaper is in need of being changed without directly inspecting inside the diaper for urination (see JP 2004-512425A and JP 2005-261466A).

DISCLOSURE OF THE INVENTION

The technique disclosed in JP 2004-512425A supra comprises color change of an initially colored wetness indicator. The problem with this technique is that a design if provided on the diaper surface may be hidden or smudged by the wetness indicator.

The technique of JP 2005-261466A supra uses a colorless wetness indicator that develops a color upon contacting a body fluid. Although it is less likely that the wetness indicator hides or smudges a design on the diaper surface, there is room for improvement in rapidness of color appearance in response to wetness.

There is a report with a disposable nonwoven fabric absorbent article equipped with a conventional wetness indicator that the wetness indicator develops a color with humidity and becomes useless while the article is not wetted with urine. Another report says that a conventional wetness indicator is not easy to apply due to its very low viscosity.

The present invention provides an absorbent article having a wetness indicator composition that has thermoplasticity and flexibility, is initially colorless in hue, and develops a bright color in rapid response to wetness with water, but does not respond to moisture absorption.

The present invention relates to an absorbent article including a topsheet, a backsheet, and an absorbent member interposed between the two sheets and having applied thereon a hot-melt composition that changes color on contact with a body fluid. The hot melt composition contains (a) 0.1% to 5% by weight of a pH indicator that is substantially colorless at pH 7 and develops a color in an acidic environment; (b) 20% to 90% by weight of a surfactant, (c) 5% to 55% by weight of a polyalkylene glycol, (d) 0% to 70% by weight of a polymer having a carboxyl group, and (e) 0.1% to 5% by weight of an acidic substance other than components (b) and (d).

The invention also relates to a package having the above described absorbent article packaged in a packaging material having a titanium content of less than 8% by weight.

BRIEF DESCRIPTION OF THE DRAWING

FIG. 5(a), FIG. 5(b), FIG. 5(c), FIG. 5(d), FIG. 5(e), FIG. 5(f) and FIG. 5(g) present plan views of application patterns of a hot melt composition (patterns of formation of a wetness indicator) applicable to the absorbent articles of the invention.

DETAILED DESCRIPTION OF THE INVENTION

Figure 1:
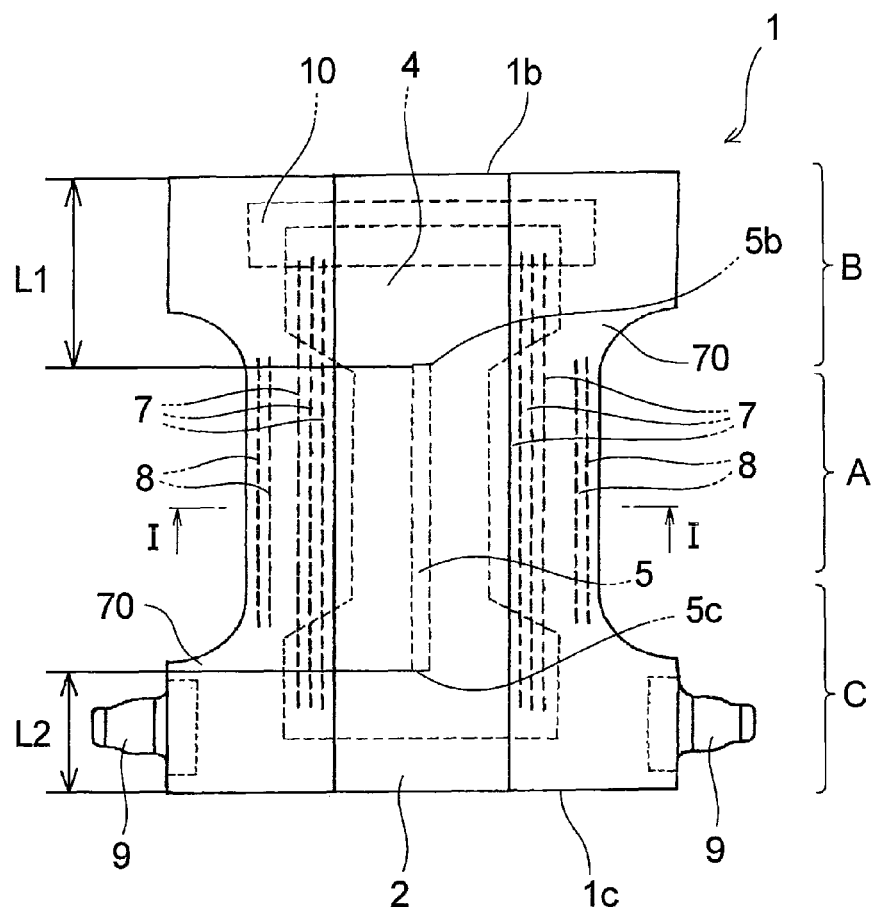
FIG. 1 is plan of a flat-type or taped disposable diaper as a first embodiment of the absorbent article of the invention, the diaper being in the stretched out state, seen from its skin facing side.

(a) pH Indicator Substantially Colorless at pH 7 and Developing Color in Acidic Environment The pH indicator used as component (a) in the wetness indicator composition of the present invention, which is substantially colorless at pH 7 and develops color in an acidic environment, (hereinafter "pH-indicator (a)") serves for color development of the wetness indicator composition.

It is preferred to use, as a pH indicator (a), a compound having a lactone structure, which is generally termed "a color former", for its light color before being wetted and for the brightness of the color developed after being wetted.

The amount of the pH indicator (a) in the wetness indicator composition is preferably 0.1% to 5% by weight, more preferably 0.5 to 2.5% by weight, based on the weight of the wetness indicator composition. If the amount of the pH indicator (a) is less than 0.1% by weight, coloration after wetting is poor in brightness. If the amount is more than 5% by weight, the color before contact with wetness is unfavorably dark.

(b) Surfactant

The surfactant (b) that can be used in the wetness indicator composition serves to help the other components be dispersed and to have a hydrophilic substance and a hydrophobic substance mixed uniformly.

Types of the surfactant (b) include anionic surfactants, nonionic surfactants, cationic surfactants, and amphoteric surfactants. Examples of the anionic surfactants include alkylsulfuric ester salts, polyoxyethylene alkyl ether sulfuric ester salts, alkylbenzenesulfonates, fatty acid salts, and naphthalenesulfonic acid-formalin condensates. Examples of the nonionic surfactants include polyoxyethylene alkyl ethers, sorbitan fatty acid esters, polyoxyethylene sorbitan fatty acid esters, polyoxyethylene sorbitol fatty acid esters, glycerol fatty acid esters, polyoxyethylene fatty acid esters, polyoxyethylene hydrogenated castor oil, polyoxyethylene alkylamines, and alkylalkanolamides. Examples of the cationic surfactants are alkylamine salts and quaternary ammonium salts. Examples of the amphoteric surfactants are alkyl betaines and alkyl aminoxides.

The surfactant (b) is preferably a nonionic surfactant in view of stability of dispersion with other components, color before wetting, and color developing properties after contact with wetness. A polyoxyalkylene alkyl ether or a polyoxyethylene derivative is particularly preferred.

The amount of the surfactant (b) in the wetness indicator composition is preferably 20% to 90% by weight, more preferably 45% to 65% by weight, based on the weight of the wetness indicator composition. When the amount of the surfactant (b) is less than 20% by weight, dispersion stability with other components is reduced, and the initial color is unsatisfactory. Use of more than 90% by weight of the surfactant (b) results in reduction of coating properties due to reduction of viscosity and also results in reduction of moisture resistance.

(c) Polyalkylene Glycol

The polyalkylene glycol (c) used in the wetness indicator composition of the invention serves to improve moisture resistance and control a response time in color development of the wetness indicator composition.

Examples of the polyalkylene glycol (c) include polyethylene glycol and polypropylene glycol.

The amount of the polyalkylene glycol (C) in the wetness indicator composition is preferably 5% to 55% by weight, more preferably 10% to 20% by weight, based on the weight of the wetness indicator composition. With less than 5% by weight of the polyalkylene glycol (C), the wetness indicator composition has reduced moisture resistance. When the amount exceeds 55% by weight, the moisture resistance reduces, too.

(d) Polymer Having Carboxyl Group (Carboxyl-Containing Polymer)

The carboxyl-containing polymer (d) used in the wetness indicator composition functions to improve the moisture resistance and control the viscosity of the wetness indicator composition. An alkylene-acrylic acid copolymer is preferred in terms of compatibility with other materials.

Examples of the carboxyl-containing polymer (d) include EAA (ethylene-acrylic acid copolymer), EMAA (ethylene-methyl acrylate copolymer), and EMA (ethylene-methyl methacrylate copolymer).

The amount of the carboxyl-containing polymer (d) to be used in the wetness indicator composition is preferably 0% to 70% by weight, more preferably 20% to 60% by weight, based on the weight of the wetness indicator composition. When the amount of the polymer (d) is more than 70% by weight, the color before wetting is unfavorably dark.

(e) Acidic Substance Other than Components (b) and (d)

The acidic substance other than components (b) and (d) (hereinafter "acidic substance (e)") that can be used in the wetness indicator composition of the invention is a color developer serving for color development of the pH indicator (a) on wetting.

Examples of the acidic substance (e) include citric acid, succinic acid, gluconic acid, lactic acid, fumaric acid, malic acid, tartaric acid, acetic acid, formic acid, uric acid, hydrochloric acid, sulfuric acid, phosphoric acid, and nitric acid.

The acidic substance (e) is preferably solid at 25° C. in view of the hue before the wetness indicator composition is wetted.

The acidic substance (e) is preferably solid at 23° C. to ensure the function of signaling wetness.

The amount of the acidic substance (e) to be used in the wetness indicator composition is preferably 0.1 to 5% by weight, more preferably 0.5 to 1.5% by weight, based on the weight of the wetness indicator composition. With less than 0.1% by weight of the acidic substance (e), the color development after wetting is weak. With more than 5% by weight of the acidic substance (e), the color before wetting is too dark.

It is preferred that each of the surfactant (b), polyalkylene glycol (c), and carboxyl-containing polymer (d) composing the wetness indicator composition have a ring and ball (R & B) softening point of 130° C. or lower in order to secure coating properties in low temperatures and to prevent thermal deterioration.

The method for measuring an R & B softening point is specified in JIS K6863-1944.

The absorbent article of the present invention, which has the above described wetness indicator composition, will then be described based on its preferred embodiments with reference to the accompanying drawing.

Figure 2:
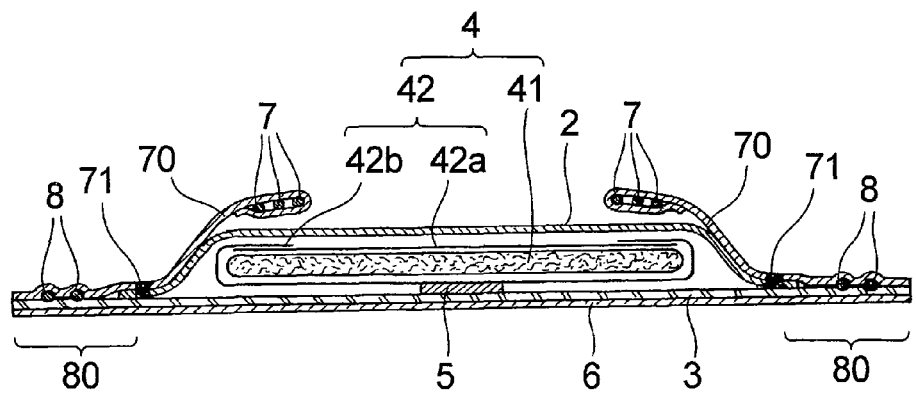
FIG. 2 is a schematic cross-section taken along line I-I of FIG. 1.

FIG. 1 illustrates a flat type or taped disposable diaper as a first embodiment of the absorbent article. FIG. 2 is a cross-section taken along line I-I of FIG. 1.

A diaper 1 of the first embodiment includes a liquid permeable topsheet 2, a moisture permeable and liquid impermeable backsheet 3, and a liquid retentive absorbent member 4 interposed between the sheets 2 and 3. As illustrated in FIG. 1, the diaper 1 is substantially oblong and has a crotch portion A in the longitudinal middle thereof, a front portion B adjacent to and forward of the crotch portion A, and a rear portion C adjacent to and backward of the crotch portion A. While worn, the crotch portion A is located at the crotch of a wearer, the front portion B and the rear portion C are located in front of and in rear of the wearer, respectively. The crotch portion A corresponds to the middle portion when the diaper is divided in three equal portions in the longitudinal direction.

The diaper 1 generally has a sandglass-like outline with its longitudinal middle portion (where the crotch portion A is located) narrowed in its stretched out state as illustrated in FIG. 1. The topsheet 2 and the backsheet 3 extend outward from both lateral side edges and both longitudinal ends of the absorbent member 4 and are bonded together in their extensions by bonding means, such as an adhesive. The backsheet 3 defines the sandglass-like outline of the diaper 1. The topsheet 2 is smaller in size than the backsheet 3 in their width direction. Both the lateral side edges of the topsheet 2 (in laterally opposing sides of the diaper) are positioned inboard of the lateral side edges of the backsheet 3 (in laterally opposing sides of the diaper).

The absorbent member 4 includes a liquid retentive absorbent core 41 and liquid permeable cover sheets 42 wrapping the absorbent core 41. The absorbent core 41 is made up of an absorbent material, such as pulp fiber or an absorbent polymer. The absorbent core 41 is substantially oblong and is generally sandglass-shaped with its longitudinal middle region narrowed in a plan view. The absorbent core 41 is covered with the cover sheets 42 on its surface except both the longitudinal end faces thereof. The cover sheets 42 thus wrap the absorbent core 41 to retain the shape of the absorbent core 41 and to prevent fall-off of a constituent of the absorbent core 41, such as an absorbent polymer. The absorbent member 4 is placed in the laterally middle region of the diaper with its longitudinal direction coincident with the longitudinal direction of the diaper.

The cover sheet 42 includes two sheets of different sizes. One of them is an upper cover sheet 42a, which has the same size with the absorbent core 41 in both the longitudinal and lateral directions of the absorbent core 41. As used herein, the term "size in the lateral direction of the absorbent core 41" means the maximum size in the lateral direction. The other is a lower cover sheet 42b, which has the same length as the length of the upper cover sheet 42a or the absorbent core 41 but is wider than the upper cover sheet 42a. The upper cover sheet 42a is disposed to face the skin facing side of the absorbent core 41. The lower cover sheet 42b is disposed to face the garment facing side of the absorbent core 41, and its side portions extending outward from both side edges of the absorbent core 41 are wrapped around to cover the upper cover sheet 42a covering the skin facing side of the absorbent core 41. The upper cover sheet 42a is bonded to the skin facing side of the absorbent core 41, and the lower cover sheet 42b is bonded to the garment facing side of the absorbent core 41, both by bonding means, such as a pressure sensitive adhesive.

The term "longitudinal direction" as used for any member refers to a direction parallel to the long side of the member, and the term "lateral direction" as used for any member refers to a direction perpendicular to the longitudinal direction of the member.

The term "skin facing side" as used for any member refers to a side of the member that is adapted to face the skin of a wearer while in use, and the term "garment facing side" as used for any member refers to a side of the member that is adapted to face a wearer's garment while in use.

The diaper 1 of the first embodiment has a hot melt composition that changes its color on contact with a body fluid, such as urine, feces, or blood. The hot melt composition is applied between the backsheet 3 and the absorbent member 4 (i.e., the lower cover sheet 42b) to provide an indicator 5. The indicator 5 (the hot melt composition) is colorless or white, namely substantially colorless, and has a function of changing in color on contact with a body fluid (color changing function). The indicator 5 functions not only as an indicator indicating to a caregiver (e.g., a mother) excretion of a body fluid from a wearer (e.g., an infant) but also as bonding means for bonding the backsheet 3 and the absorbent member 4. The indicator 5 may be formed by applying the hot melt composition to either the skin facing side of the backsheet 3 or the garment facing side of the absorbent member 4 (i.e., the lower cover sheet 42b).

The indicator 5 (hot melt composition) is formed continuously between the backsheet 3 and the absorbent member 4 (i.e., the lower cover sheet 42b) in the laterally middle region of the crotch portion A over the whole length (in the diaper longitudinal direction) of the crotch portion A. The position of the indicator 5 is preferably such that a caregiver may easily recognize the indicator 5 from either the rear side or the front side of the diaper when a wearer wearing the diaper is lying on its stomach or back. In application to, for example, diapers for babies, the indicator 5 has a strip shape preferably with a length of 30 to 200 mm, more preferably 50 to 150 mm, and a width of 2 to 300 mm, more preferably 5 to 20 mm.

The shortest distance L1 between the longitudinally front end 5b of the indicator 5 and the longitudinally front end 1b of the front portion B of the diaper 1 is preferably 20% to 40%, more preferably 25% to 30%, of the total length of the diaper 1.

The shortest distance L2 between the longitudinally rear end 5c of the indicator 5 and the longitudinally rear end 1c of the rear portion C of the diaper 1 is preferably 20% to 40%, more preferably 20% to 30%, of the total length of the diaper 1.

The hot melt composition making the indicator 5 is the above described wetness indicator composition according to the present invention. That is, the hot melt composition making the indicator 5 contains (a) 0.1% to 5% by weight of a pH indicator that is substantially colorless at pH 7 and develops a color in an acidic environment; (b) 20% to 90% by weight of a surfactant, (c) 5% to 55% by weight of a polyalkylene glycol, (d) 0% to 70% by weight of a polymer having a carboxyl group, and (e) 0.1% to 5% by weight of an acidic substance other than components (b) and (d), the total amount of compounds (a) to (e) being taken as 100% by weight. The description given above about components (a) to (e) applies to the hot melt composition.

The indicator 5 (hot melt composition) having a color changing function is colorless or white, i.e., substantially colorless and rapidly changes its color upon contacting a body fluid. The color to which the indicator 5 changes may be chosen freely from a plurality of hues through appropriate selection of the pH indicator (a). For instance, choosing 3,3-bis(p-dimethylaminophenyl)-6-dimethylaminophthalide as component (a) enables color change to blue. The choice of 3,6-bis(diethylamino)fluoran-γ-(4'-nitro)-anilinolactam as component (a) achieves change to red. Change to green may be achieved by using 2-N,N-dibenzylamino-6-diethylaminofluoran as the pH indicator (a).

It is desirable that the indicator 5 (hot melt composition) show a rapid response to a body fluid. Specifically, it is desired for the indicator 5 to change its color within 1 minute from the contact with a body fluid. Such a rapid response to a body fluid is secured by using the aforementioned wetness indicator composition of the invention as the hot melt composition.

The indicator 5 (hot melt composition) having changed its color on being wetted with a body fluid returns to its initial color when dried. After the indicator 5 once wetted is dried to return to its initial color, it is able to change in color on being wetted again. That is, the indicator 5 is capable of reversible color change between a wetted, colored state and a dried, substantially colorless state. Such reversibility of color change is not possessed by a conventional absorbent article having an indicator function of this type. In a conventional absorbent article with wetness indicator, the indicator does not return to its original color even when dried after it changes its color (or develops a color) on being wetted. If a conventional absorbent article with a wetness indicator changes the color of the indicator by exposure to moisture, for example, moisture in the air, it must be disposed of in spite of being unused. In contrast to this, the diaper 1 of the present embodiment is free from such a disadvantage because the color change of the indicator 5 is reversible. That is, even if the indicator 5 undergoes color change due to, for instance, moisture in the air before use, it is able to return to its original color (substantially colorless state) by drying. The above-mentioned color change reversibility is obtained by using the wetness indicator composition of the invention as the hot melt composition.

It is preferred that the hot melt composition providing the indicator 5 be excellent in heat resistance, more specifically, capable of retaining the color changing function even after being heated continuously at 130° C. for 24 hours. The phrase "capable of retaining the color changing function" as used herein is intended to mean that the hot melt composition having been heated under the conditions recited above is able to change in color again upon contacting a body fluid in the same fashion as before the heating.

Such excellent heat resistance can be secured by using the wetness indicator composition of the invention as the hot melt composition.

It is preferred that the hot melt composition providing the indicator 5 be excellent in moisture resistance, more specifically, capable of retaining the color changing function even after being left to stand in an environment at 40° C. and 80%

RH for 24 hours. The phrase "capable of retaining the color changing function" as used herein is intended to mean that the hot melt composition having been left to stand under the conditions recited above is able to change in color again upon contacting a body fluid in the same fashion as before the heating.

Such excellent moisture resistance can be secured by using the wetness indicator composition of the invention as the hot melt composition.

The hot melt composition providing the indicator 5 preferably has a softening point of 75° to 100° C., more preferably 75° to 90° C., to have improved coating properties in low temperatures.

The hot melt composition providing the indicator 5 preferably has a viscosity adjustable between 20 and 12000 mPa·s, more preferably between 2000 and 8000 mPa·s, when heated to 80° to 130° C. Conventional hot melt compositions used in this type of diapers generally have a viscosity ranging from 1000 to 2000 mPa·s at a temperature of 80° to 130° C. In other words, they have a narrower range of viscosity adjustment, which has restricted the coating techniques, limited the application patterns to simple ones, such as a straight line pattern or a simple design, and caused the hot melt composition to splash when applied or to result in poor coating quality. In contrast to this, use of the hot melt composition with its viscosity adjustable in the range of from 20 to 12000 mPa·s at 80° to 130° C. offers broader choice of coating techniques including various coating methods considered inapplicable to conventional hot melt compositions, such as ink jet printing, enables formation of complicated application patterns, and prevents the splash or poor coating quality problems associated with the conventional hot melt compositions.

The above recited viscosity range (20 to 12000 mPa·s) can be obtained by using the wetness indicator composition of the invention as the hot melt composition.

The indicator 5 is formed by applying the hot melt composition to a prescribed part, followed by, if desired, drying. The hot melt composition may be applied by any method selected from known coating techniques, including contact application systems (in which an applicator is in contact with a surface to be coated) and non-contact application systems (in which an applicator is in non-contact with a surface to be coated). For example, various contact type coaters, such as a roll coater, and non-contact applicators, such as a bead gun, a spiral gun, a summit gun, an omega gun, a spray gun, a comb gun, and an inkjet applicator may be used.

The amount of the indicator 5 (the amount of the hot melt composition to be applied) is preferably 10 to 50 g/m$^2$, more preferably 15 to 25 g/m$^2$, in view of avoiding uneven application.

The diaper 1 of the first embodiment will further be described.

The backsheet 3 is provided on its garment facing side with an exterior sheet 6 formed of nonwoven fabric. The backsheet 3 and the exterior sheet 6 are bonded by bonding means, such as an adhesive. The exterior sheet 6 has the same shape as the backsheet 3.

The diaper 1 has a pair of standing cuffs that are designed to rise up along the laterally opposite sides of the absorbent member 4. The standing cuffs are each formed of a cuff-forming sheet 70 elasticized with an elastic member 7 and provided along each lateral side of the diaper 1.

The cuff-forming sheet 70 has one or more elastic members 7 (three elastic members in the first embodiment) fixed along its free edge in their stretched state. The sheet 70 is bonded to the topsheet 2 along a bond 71 extending in the diaper longitudinal direction at a position outboard of the lateral side edge of the absorbent member 4. The bond 71 provides a base 71 from which the cuff rises up. The sheet 70 extends laterally outward from the base 71, and the extension is bonded to the backsheet 3. The sheet 70 is bonded to the topsheet 2 on its longitudinally front and rear end portions.

The backsheet 3 and the exterior sheet 6 extend laterally outward from the base 71 (bond 71) of each standing cuff to form a leg flap 80 extending in the crotch portion A in the diaper longitudinal direction. The leg flap 80 is elasticized with one or more leg elastic members 8 (two in the first embodiment) fixed along near the free edge thereof in their stretched state. The leg elastic members 8 are disposed between the backsheet 3 and the cuff-forming sheet 70 and are not in contact with the topsheet 2. The leg elastic members are disposed over the whole length of the crotch portion A in the diaper longitudinal direction.

A pair of fastening tapes 9 are provided on both lateral sides of the rear portion C of the diaper 1. A landing zone 10 on which the fastening tapes 9 are to be secured is provided on the garment facing side (on the surface of the exterior sheet 6) of the rear portion C of the diaper 1. The fastening tape 9 is formed of a tape base and a male member of a mechanical fastener bonded to one side of the tape base. Any male member known in the art may be used. The landing zone 10 may be formed of a base sheet of nonwoven fabric or resin film and a female member of a mechanical fastener bonded to the base sheet. The female member may be of any material to which the male member can be pressed to be secured.

The topsheet 2 may be of any material that has been used in this type of diapers and allows passage of liquid, such as urine, including woven and nonwovens fabrics made of synthetic fibers or natural fibers and porous sheets. The topsheet 2 is exemplified by a nonwoven fabric fabricated by carding core/sheath (inclusive of side-by-side configuration) conjugate fibers having a polypropylene or polyester core and a polyethylene sheath into a web and consolidating the carded web by through-air bonding, followed by, if desired, perforation. A perforated sheet made of a polyolefin, such as low-density polyethylene, is also suitable for its high liquid permeability (dry feel). The topsheet 2 preferably has a basis weight of 20 to 50 g/m$^2$.

The backsheet 3 may be of any material that has been used in this type of diapers. A liquid impermeable or water repellent and moisture permeable sheet is used preferably. Examples of the backsheet 3 include a liquid impermeable or water repellent porous resin film (e.g., of polyethylene, polypropylene, or polyethylene terephthalate), a liquid impermeable or water repellent nonwoven fabric, and a laminate of the porous resin film and the nonwoven fabric. Examples of the liquid permeable or water repellent nonwoven fabric include thermally bonded nonwoven, spun bonded nonwoven, spun bonded/melt blown/spun bonded (SMS) nonwoven, and spun bonded/melt blown/melt blown/spun bonded (SMMS) nonwoven. The backsheet 3 preferably has a basis weight of 10 to 20 g/m$^2$.

The exterior sheet 6 provided on the garment facing side of the backsheet 3 is preferably formed of a liquid impermeable or water repellent nonwoven fabric, a porous resin film, and so on, which are also preferred for use as the backsheet 3. The exterior sheet 6 preferably has a basis weight of 15 to 35 g/m$^2$.

The absorbent core 41 providing the absorbent member 4 may be any of the kinds that have conventionally been used in this type of diapers. Any type capable of absorbing liquid such as urine may be used, exemplified by an absorbent substance, such as an absorbent polymer or ground pulp, sandwiched between absorbent paper sheets or nonwoven fabric sheets. The absorbent polymer may be used as mixed with pulp, or spread on the side of the backsheet 3, or inserted in the form of a layer in the middle of the thickness of the absorbent core. The absorbent polymer may be disposed in parts in the form, e.g., of a polymer sheet made by known means. Synthetic fibers or bulky pulp fibers obtained by, for example, crosslinking treatment may be incorporated into the absorbent member 4 to improve resilience of a compressed part of the absorbent member when the compressed part absorbs a body fluid. The absorbent polymer is not essential. Various absorbent polymers that have been used in this type of diapers can be used, including sodium polyacrylate, acrylic acid-vinyl alcohol copolymers, crosslinked sodium polyacrylate, starch-acrylic acid copolymers, isobutylene-maleic anhydride copolymers and saponification products thereof, potassium polyacrylate, and cesium polyacrylate. These absorbent polymers may be used individually or as a mixture of two or more thereof.

The cover sheets 42 (including the upper cover sheet 42a and the lower cover sheet 42b) making the absorbent member 4 may be of any kind that has been used in this type of diapers. Liquid permeable sheets, such as fiber sheets and perforated films, are used preferably. Hydrophilic fiber sheets, including paper (e.g., tissue) and various nonwoven fabrics, are more preferred for their good liquid permeability. The nonwoven fabrics include those made up of hydrophilic fibers, such as cotton or rayon, and those made of hydrophilized synthetic resin fibers. Examples of the nonwoven fabrics are spun bonded, spun lace, air-laid, or air-through nonwoven fabrics having been treated with a surface active agent. The cover sheets 42 each preferably have a basis weight of 12 to 20 g/m$^2$.

The elastic members 7 and 8 may be of any kind that has been used in this type of diapers, including elastic threads or tapes of olefin rubber, urethane rubber, styrene rubber, or polyurethane and urethane foam tapes.

The diaper 1 of the first embodiment is used in the same manner as ordinary flat type diapers. Having the indicator 5 made of the hot melt composition containing components (a) to (e), the diaper 1 rapidly sends a signal of a discharge of a body fluid, such as urine, feces or blood, to a caregiver. Since the indicator 5 is substantially colorless (colorless or white) before contact with a body fluid, a design, if printed to overlap the indicator 5, will not be hidden or smudged by the indicator 5 so that the printing may be designed freely without giving consideration to the indicator.

Since the indicator 5 has color change reversibility and repeatedly changes in color between a wet state and a dry state, in the event that the indicator 5 undergoes color change by the moisture in the atmosphere before use, it is possible for the indicator 5 to fade back to its original color by drying it. Thus, the waste of disposing of an unused diaper is avoided to save the production cost. Furthermore, the indicator 5 retains its color changing function stably in an extended period of time because of its superior resistance to heat, moisture, and weather (light).

Since the hot melt composition forming the indicator 5 has a viscosity adjustable in a wider range of from 20 to 12000 mPa·s at 80° to 130° C. than conventional hot melt compositions, various coating methods can be used to apply the composition, and a wide variety of application patterns, such as straight lines, curved lines, figures, and letters, can be formed by a properly selected coating method. The splash of the hot melt composition during application or the poor coating quality problem can be prevented, leading to improvement of diaper quality (reduction of complaints about the product). The wide range of choice of application patterns and the wide range of choice of colors to be developed allow a manufacturer to tailor the diaper design such that a caregiver and a wearer may enjoy changing diapers.

Other embodiments of the absorbent article according to the invention will then be described. The description will generally be confined to the differences from the diaper 1 of the first embodiment. Thus common parts are identified by the same numerals as in the previously described embodiment and will not be redundantly described. The description on the first embodiment applies to the embodiments described hereunder unless otherwise specified.

Figure 3:
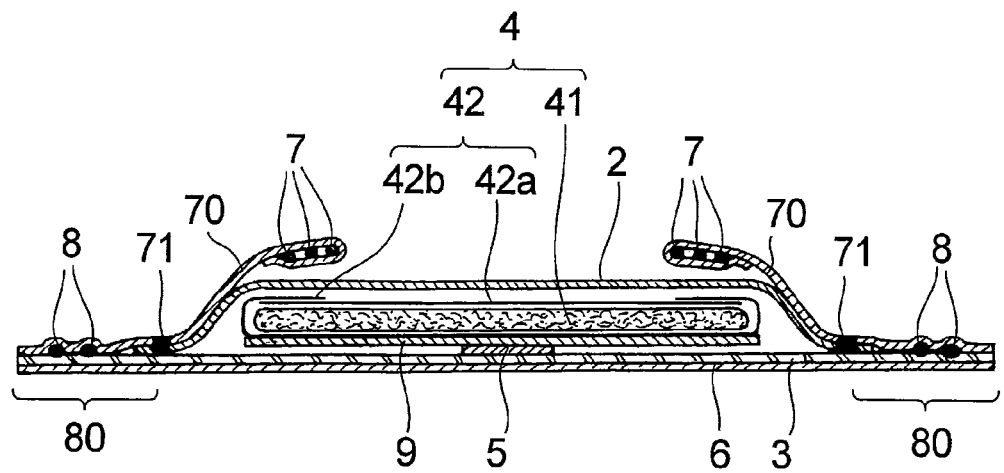
FIG. 3 illustrates another flat type disposable diaper as a second embodiment of the absorbent article of the invention (equivalent to FIG. 2).

FIG. 3 illustrates a second embodiment of the invention. The diaper of the second embodiment has an intermediate sheet 9 between the backsheet 3 and the absorbent member 4, and the hot melt composition is applied between the backsheet 3 and the intermediate sheet 9 to provide the indicator 5. More specifically, the indicator 5 (hot melt composition) is applied continuously between the backsheet 3 and the intermediate sheet 9 in the laterally middle region of the crotch portion A over the whole length of the crotch portion A in the diaper longitudinal direction. The hot melt composition may be applied to either the skin facing side of the backsheet 3 or the garment facing side of the intermediate sheet 9.

The intermediate sheet 9 is used chiefly as a subsheet that prevents urine leakage from the absorbent member or absorbs leaked urine or for emblazoning the diaper with an attractive design. The intermediate sheet 9 is rectangular with its width almost equal to the width (maximum width) of the absorbent member 4 and its length almost equal to the length of the absorbent member 4. The absorbent member 4 and the intermediate sheet 9 are joined to each other by bonding means, such as an adhesive. Examples of the intermediate sheet 9 are film, water repellent nonwoven, hydrophilic nonwoven, and tissue. The intermediate sheet 9 preferably has a basis weight of 10 to 50 g/m$^2$.

The second embodiment having the above described configuration produces the same effects as the first embodiment.

Figure 4:
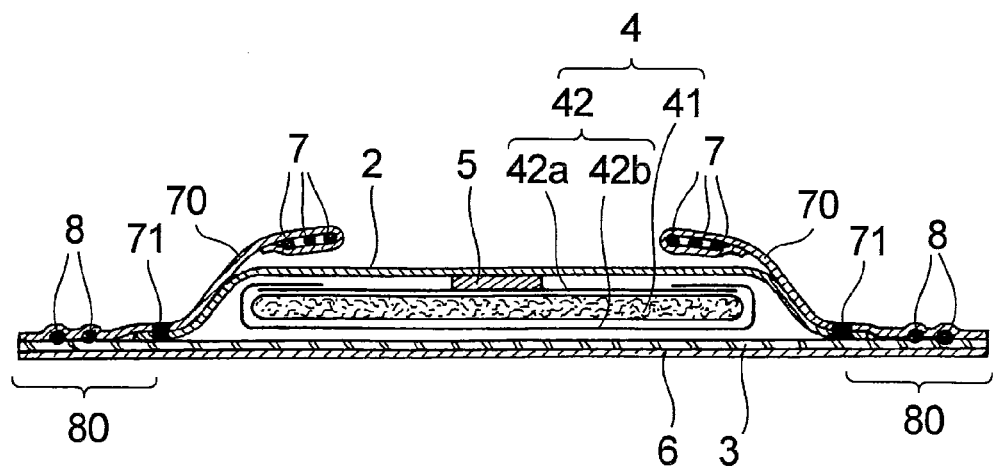
FIG. 4 illustrates still another flat type disposable diaper as a third embodiment of the absorbent article of the invention (equivalent to FIG. 2).

FIG. 4 illustrates a third embodiment of the invention, in which the hot melt composition is applied between the topsheet 2 and the absorbent member 4 (the upper cover sheet 42a) to form the indicator 5. More specifically, the indicator 5 (hot melt composition) of the third embodiment extends continuously between the topsheet 2 and the absorbent member 4 in the laterally middle region of the crotch portion A over the whole length of the crotch portion A in the diaper longitudinal direction. To form the indicator 5, the hot melt composition may be applied either to the garment facing side of the topsheet 2 or the skin facing side of the absorbent member 4 (the upper cover sheet 42a).

The third embodiment having the above described configuration produces the same effects as the first embodiment. In addition, the indicator 5 of the third embodiment changes in color in response to even a small amount of a body fluid excreted because it is closer to the wearer's crotch than the absorbent member 4. Therefore, the indicator 5 sends a signal recognizable from outside the diaper, indicating a presence of even a small amount of a body fluid.

In the present invention, the hot melt composition may be applied to any part of an absorbent article where a body fluid, such as urine, feces or blood passes through. The place to apply the hot melt composition, i.e., the place to form the indicator 5 is not limited to those in the above described embodiments.

For instance, the invention provides a fourth embodiment in which the hot melt composition may be applied between the backsheet 3 and the exterior sheet 6. More specifically, the hot melt adhesive is continuously applied between the backsheet 3 and the exterior sheet 6 in the laterally middle region of the crotch portion A over the whole length of the crotch portion A in the diaper longitudinal direction. The hot melt adhesive may be applied either to the garment facing side of the backsheet 3 or the skin facing side of the exterior sheet 6.

Because the indicator 5 of the fourth embodiment is positioned closer to the outside of the diaper in use than in any of the first to third embodiments, there is produced the effect that the color change of the indicator 5 is easily recognizable from outside the diaper by a caregiver.

In the case where the diaper has a standing cuff on both the opposite lateral sides of the absorbent member 4 as in the aforementioned embodiments, the hot melt composition may be applied to the elastic members 7 used to make the standing cuff rise up. In this case, the elastic members 7 of the standing cuffs function as an indicator indicating a discharge of a body fluid.

The hot melt composition may be applied to a combination of a plurality of parts of a diaper. The parts hereinabove described where to apply the hot melt composition (where to form an indicator 5) may be combined appropriately. For instance, the diaper of each of the first to fourth embodiments may have the hot melt composition additionally applied to the surface of the elastic members 7 for the standing cuffs.

The application pattern of the hot melt composition is not limited to a single strip as in the foregoing embodiments and may be readily designed using straight lines, curved lines, figures, letters, and the like. FIG. 5 represents examples of hot melt composition (indicator 5) application patterns applicable to the present invention. All the embodiments illustrated in FIG. 5 have the hot melt composition applied to the skin facing side of the backsheet 3. The topsheet 2, the absorbent member 4, and the standing cuffs are omitted from FIG. 5 for the sake of ease of illustration. The hot melt composition application patterns illustrated in FIG. 5 are applicable to the other embodiments in which the hot melt composition is applied to the other members of the diaper, such as the topsheet 2, the absorbent member 4, or the exterior sheet 6.

The embodiment illustrated in FIG. 5(a) has a plurality of (five in FIG. 5(a)) hot melt composition-applied portions (indicators) 5a, 5b, and 5c extending in the diaper longitudinal direction and spaced parallel in the diaper lateral direction. The indicators comprise a middle indicator 5a positioned in the middle of the diaper width and a plurality of indicators 5b and a plurality of indicators 5c bilaterally symmetrical about the middle indicator 5a. The middle indicator 5a is different in color developed from the other indicators 5b and 5c. The indicators 5b and the indicators 5c are different in color developed according to the distance from the middle indicator 5a. That is, the middle indicator 5a, the pair of indicators 5b at a certain distance from the middle indicator 5a, and the pair of indicators 5c outboard of the indicators 5b are different in color developed. Such a configuration makes it possible for a caregiver to know the distribution of a body fluid excreted in the diaper and to catch a sign of leakage beforehand.

The embodiment illustrated in FIG. 5(b) has the same configuration as the embodiment of FIG. 5(a), except that the indicators 5a, 5b, and 5c extend in the diaper lateral direction and spaced parallel to each other in the diaper longitudinal direction. The embodiment of FIG. 5(b) produces the same effect as the embodiment of FIG. 5(a).

The embodiments illustrated in FIGS. 5(c) and 5(d) are examples in which the hot melt composition (indicator 5) is applied to form a figure pattern. The embodiment illustrated in FIG. 5(e) is an example in which the hot melt composition is applied in letters. The embodiments of FIGS. 5(f) and 5(g) are examples having a pattern composed of a combination of a figure(s) and letters.

The package of absorbent articles according to the present invention will then be described based on its preferred embodiments with reference to the accompanying drawing.

Figure 6A:
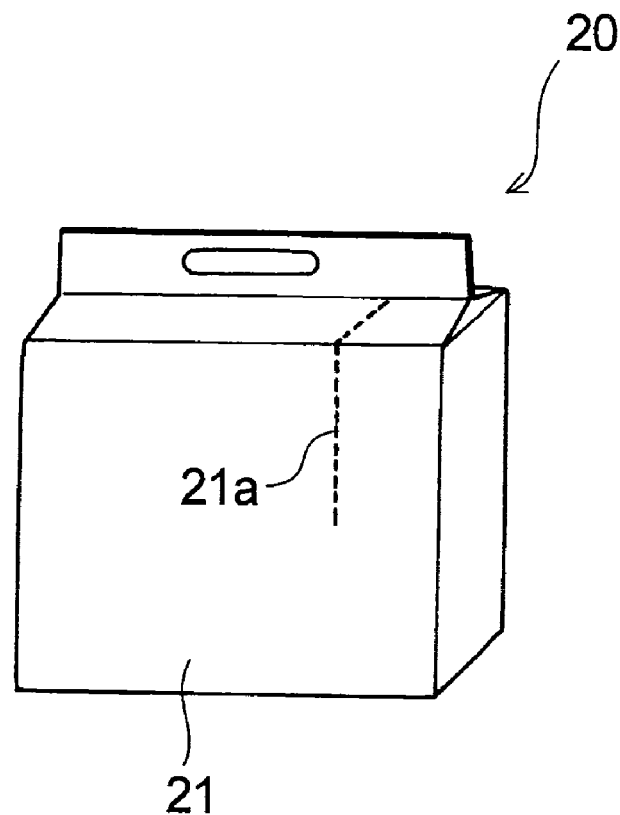
FIG. 6(a) is a perspective of an embodiment of the package of absorbent articles according to the invention.
Figure 6B:
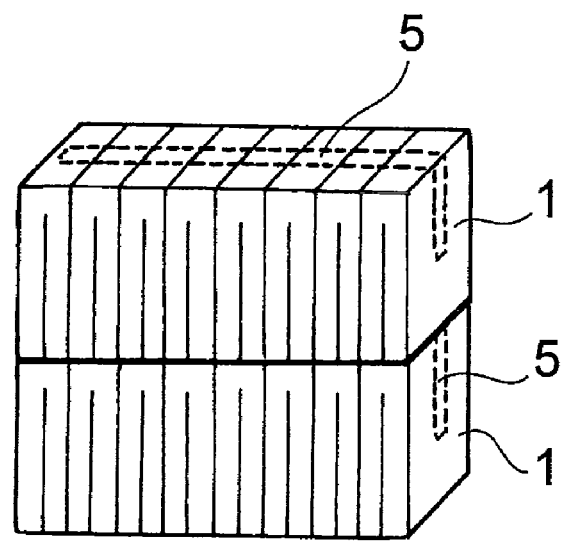
FIG. 6(b) is a perspective of the contents (stacks of diapers) of the package illustrated in FIG. 6(a).

FIG. 6 illustrated an embodiment of the package of disposable diaper according to the invention. FIG. 6(a) is a perspective of the package of the present embodiment, and FIG. 6(b) is a perspective of the contents (stacks of diapers) of the package of FIG. 6(a).

The package 20 of the present embodiment is composed of the diapers 1 of the first embodiment packaged in a packaging material 21. The package 20 contains a plurality of diapers 1 having the indicator 5 in their folded and stacked state. The packaging material 21 is of a conventional material commonly used in this type of package structures, such as polyethylene. The packaging material 21 has perforations 21a for easy opening. The above described package structure is conventional.

A conventional package of conventional diapers with wetness indicator has an objection that a diaper whose indicator has changed in color due to moisture having entered inside the package through the perforations or an insufficient seal must be disposed of as a reject. The package 20 of the present embodiment is free from such a problem because, even if the indicator 5 of the diaper 1 in the package undergoes color change due to wetness, it is able to return to its original color on being dried.

A conventional wetness indicator of conventional diapers with indicator has poor weatherability (light resistance) and undergoes color change with time when exposed to open air and light. To prevent this, the packaging material used in the package needs to contain 7% to 8% by weight of titanium, which entails an increase in production cost. In contrast, the indicator 5 of the diapers 1 in the package 20 of the present embodiment exhibits excellent weatherability (light resistance). This permits to reduce the amount of titanium, which has caused an increase in material cost, as compared with the conventional packaging material, resulting in a lower cost to product the package. The titanium content in the packaging material 21 used in the present embodiment is preferably less than 8% by weight, more preferably 3% to 5% by weight. As used herein, the term "titanium" refers to titanium oxide, which is usually contained in a master batch. The packaging material 21 can be of any material that is commonly employed in the same type of packagings.

While the present invention has been described largely with reference to its preferred embodiments, the invention is not construed as being limited thereto. For example, the absorbent articles to which the invention is applied are not limited to flat type, taped diapers but pants type, pull-on diapers, sanitary napkins, incontinence pads, shorts covers, and absorbent briefs.

EXAMPLES

The present invention will now be illustrated in greater detail with reference to Examples, but it should be understood that the invention is not deemed to be limited thereto.

Preparation of Wetness Indicator Composition

The surfactant (b) and polyalkylene glycol (c) illustrated in Tables 1 and 2 were put in a heat-resistant glass beaker equipped with a stirrer and heated taking care not to exceed 130° C. After the contents melted, they were stirred to a uniform mixture. The carboxyl-containing polymer (d) illustrated in Tables was then slowly added thereto. Finally, the pH indicator (a) and acidic substance (e) illustrated in Tables were added to prepare a wetness indicator composition.

The pH indicators (a), surfactants (b), polyalkylene glycols (c), carboxyl-containing polymers (d), and acidic substances (e) illustrated in Tables 1 and 2 are as follows.

pH Indicators (a) that is substantially colorless at pH 7 and develops a color in an acidic environment:
(a)-1: 3,6-Bis(diethylamino)fluoran-γ-(4'-nitro)-anilinolactam (turning red in an acidic environment)
(a)-2: 2-N,N-Dibenzylamino-6-diethylaminofluoran (turning green in an acidic environment)
(a)-3: 3,3-Bis(p-dimethylaminophenyl)-6-dimethylaminophthalide (turning blue in an acidic environment)
Surfactant (b):
(b)-1: Polyoxyethylene alkylene alkyl ether (liquid at 23° C.)
(b)-2: Polyoxyethylene polyoxypropylene glycol (liquid at 23° C.)
(b)-3: Polyoxyethylene lauryl ether (softening point: 70° C.)
(b)-4: Alkylbenzylmethylammonium chloride (liquid at 23° C.)
(b)-5: Special polycarboxylic acid type polymeric surfactant (liquid at 23° C.)
Polyalkylene glycol (c):
(c)-1: Polyethylene glycol (mol. wt.: 1000; softening point: 37° C.)
(c)-2: Polyethylene glycol (mol. wt.: 3000; softening point: 53° C.)
(c)-3: Polyethylene glycol (mol. wt.: 20000; softening point: 60° C.)
(c)-4: Polypropylene glycol (mol. wt.: 3000; liquid at 23° C.)
Water soluble material (c'):
(c')-1: Polyvinyl alcohol (mol. wt.: 3000; liquid at 23° C.)
Carboxyl-containing polymer (d):
(d)-1: EAA (MFR: 1300 g/10 min; softening point: 75° C.)
(d)-2: EAA (MFR: 300 g/10 min; softening point: 82° C.)
(d)-3: EMAA (MFR: 300 g/10 min; softening point: 80° C.)
(d)-4: EMMA (MFR: 450 g/10 min; softening point: 90° C.)
Carboxyl-free polymer (d'):
(d')-1: EVA (MFR: 400 g/10 min; softening point: 70° C.)
(d')-2: SIS (MFR: 40 g/10 min)
Acidic Substance (e) Other than Components (b) and (d):
(e)-1: Citric acid
(e)-2: Succinic acid
(e)-3: Acetic anhydride Evaluation of Wetness Indicator Composition Tests (1) to (6) were carried out in accordance with the procedures described below. Each of the resulting wetness indicator compositions was applied to a backsheet to a thickness of 20 g/m² with a hand coater to make a test specimen. The backsheet used was the moisture permeable sheet (a laminate sheet having a nonwoven fabric on one side thereof) of a commercially available disposable diaper "Merries" from Kao Corp.

(1) Softening Point

The softening point was measured by the R & B method specified in JIS K6863-1944.

(2) Measurement of Viscosity

The test method (A) specified in JIS K6862 was followed. In a test container was put 300 g of the hot melt composition having been melted at a temperature 10° C. higher than the measuring temperature and thoroughly stirred with a bar thermometer. When the temperature fell to the measuring temperature, the viscosity was measured with a Brookfield viscometer (TOKIMEC Viscometer, model BM, from Toki Sangyo Co., Ltd.) fitted with an appropriately chosen rotor.

(3) Measurement of Color Change Time

The term "color change time" as used herein means the time required from wetting the specimen under a given condition to appearance of a perceptible color. Specifically, the time required for the specimen to change from colorless to perceptively colored when it was impregnated with ion exchanged water was taken as a color change time. Specimens with a color change time within 10 seconds, within 60 seconds, and 60 seconds or longer were rated "very good", "good", and "medium", respectively. A specimen that did not develop a color in an hour or longer was rated "bad".

(4) Measurement of Moisture Resistance

The specimen was inspected for color development when allowed to stand at 40° C. and 80% RH to evaluate moisture resistance. A specimen showing no color development in 48 hours, a specimen with no color development in 24 hours but showing color development in 48 hours, and a specimen that developed a color within 24 hours were rated "good", "medium", and "bad", respectively.

(5) Initial Hue Grading

The term "initial hue" as used herein is intended to mean the hue of the specimen before being wetted with water. Hues from what is recognized as colorless to a hue after color development were given three grades, "good", "medium", and "bad".

(6) Test of Color Developing Ability

The term "initial hue" as used herein is intended to mean the hue of the specimen before being wetted with water. Hues from what is recognized as colorless to a hue after color development were given three grades, "good", "medium", and "bad".

TABLE 1

| Composition | | Example No. | | | | | | | | | |
|---|---|---|---|---|---|---|---|---|---|---|---|
| | | 1 | 2 | 3 | 4 | 5 | 6 | 7 | 8 | 9 | 10 |
| pH Indicator (a) | (a)-1 | 2 | | | 2 | 2 | 2 | 2 | 2 | 2 | 2 |
| | (a)-2 | | 2 | | | | | | | | |
| | (a)-3 | | | 2 | | | | | | | |
| Surfactant (b) | (b)-1 | 47 | 47 | 47 | | | | | 47 | 47 | 47 |
| | (b)-2 | | | | 47 | | | | | | |
| | (b)-3 | | | | | 47 | | | | | |
| | (b)-4 | | | | | | 47 | | | | |
| | (b)-5 | | | | | | | 47 | | | |
| Polyalkylene Glycol (c) | (c)-1 | 15 | 15 | 15 | 15 | 15 | 15 | 15 | | | |
| | (c)-2 | | | | | | | | 15 | | |
| | (c)-3 | | | | | | | | | 15 | |
| | (c)-4 | | | | | | | | | | 15 |

TABLE 1-continued

| Composition | | 1 | 2 | 3 | 4 | 5 | 6 | 7 | 8 | 9 | 10 |
|---|---|---|---|---|---|---|---|---|---|---|---|
| Water Soluble Material (c') | (c')-1 | | | | | | | | | | |
| Carboxyl-containing Polymer (d) | (d)-1 | 35 | 35 | 35 | 35 | 35 | 35 | 35 | 35 | 35 | 35 |
| | (d)-2 | | | | | | | | | | |
| | (d)-3 | | | | | | | | | | |
| | (d)-4 | | | | | | | | | | |
| Carboxyl-free Polymer (d') | (d')-1 | | | | | | | | | | |
| | (d')-2 | | | | | | | | | | |
| Acidic Substance (e) other than (b) and (d) | (e)-1 | 1 | 1 | 1 | 1 | 1 | 1 | 1 | 1 | 1 | 1 |
| | (e)-2 | | | | | | | | | | |
| | (e)-3 | | | | | | | | | | |
| Total | | 100 | 100 | 100 | 100 | 100 | 100 | 100 | 100 | 100 | 100 |
| Test Item | Softening Point (° C.) | 80.0 | 80.0 | 80.0 | 78.0 | 81.0 | 79.0 | 79.0 | 81.0 | 81.0 | 80.0 |
| | Viscosity at 110° C. (mPa·s) | 980 | 980 | 980 | 940 | 1120 | 950 | 950 | 1070 | 1120 | 1020 |
| | Color Change Time | very good | very good | very good | very good | good | medium | medium | very good | very good | good |
| | Moisture Resistance | good | good | good | good | good | good | good | good | good | good |
| | Initial Hue | good | good | good | good | good | medium | medium | good | good | good |
| | Color Developing Properties | good | good | good | good | medium | medium | medium | good | good | good |

| Composition | | 11 | 12 | 13 | 14 | 15 | 16 | 17 | 18 |
|---|---|---|---|---|---|---|---|---|---|
| pH Indicator (a) | (a)-1 | 2 | 2 | 2 | 2 | 2 | 0.3 | 4 | 2 |
| | (a)-2 | | | | | | | | |
| | (a)-3 | | | | | | | | |
| Surfactant (b) | (b)-1 | 47 | 47 | 47 | 47 | 47 | 47.7 | 46 | 27 |
| | (b)-2 | | | | | | | | |
| | (b)-3 | | | | | | | | |
| | (b)-4 | | | | | | | | |
| | (b)-5 | | | | | | | | |
| Polyalkylene Glycol (c) | (c)-1 | 15 | 15 | 15 | 15 | 15 | 15.5 | 14.5 | 25 |
| | (c)-2 | | | | | | | | |
| | (c)-3 | | | | | | | | |
| | (c)-4 | | | | | | | | |
| Water Soluble Material (c') | (c')-1 | | | | | | | | |
| Carboxyl-containing Polymer (d) | (d)-1 | | | | 35 | 35 | 35.5 | 34.5 | 45 |
| | (d)-2 | 35 | | | | | | | |
| | (d)-3 | | 35 | | | | | | |
| | (d)-4 | | | 35 | | | | | |
| Carboxyl-free Polymer (d') | (d')-1 | | | | | | | | |
| | (d')-2 | | | | | | | | |
| Acidic Substance (e) other than (b) and (d) | (e)-1 | 1 | 1 | 1 | 1 | | | 1 | 1 |
| | (e)-2 | | | | | 1 | | | |
| | (e)-3 | | | | | | 1 | | |
| Total | | 100 | 100 | 100 | 100 | 100 | 100 | 100 | 100 |
| Test Item | Softening Point (° C.) | 82.0 | 84.0 | 83.0 | 80.0 | 80.0 | 81.0 | 81.0 | 86.0 |
| | Viscosity at 110° C. (mPa·s) | 1700 | 1750 | 1220 | 980 | 960 | 980 | 950 | 1310 |
| | Color Change Time | very good | good | medium | very good | very good | very good | very good | very good |
| | Moisture Resistance | good | good | good | good | good | good | good | good |
| | Initial Hue | good | medium | medium | good | medium | good | medium | medium |
| | Color Developing Properties | good | good | good | good | good | medium | good | good |

TABLE 2

| Composition | | Example No. | | | | | | Comparative Example No. | | |
|---|---|---|---|---|---|---|---|---|---|---|
| | | 19 | 20 | 21 | 22 | 23 | 24 | 1 | 2 | 3 |
| pH Indicator (a) | (a)-1 | 2 | 2 | 2 | 2 | 2 | 2 | 0 | 6 | 2 |
| | (a)-2 | | | | | | | | | |
| | (a)-3 | | | | | | | | | |

TABLE 2-continued

| Composition | | | | | | | | | | |
|---|---|---|---|---|---|---|---|---|---|---|
| Surfactant (b) | (b)-1 | 67 | 51 | 35 | 26 | 47.7 | 45.5 | 48 | 45 | 0 |
| | (b)-2 | | | | | | | | | |
| | (b)-3 | | | | | | | | | |
| | (b)-4 | | | | | | | | | |
| | (b)-5 | | | | | | | | | |
| Polyalkylene Glycol (c) | (c)-1 | 10 | 7 | 40 | 10 | 15 | 14.5 | 15 | 14 | 47 |
| | (c)-2 | | | | | | | | | |
| | (c)-3 | | | | | | | | | |
| | (c)-4 | | | | | | | | | |
| Water Soluble Material (c') | (c')-1 | | | | | | | | | |
| Carboxyl-containing Polymer (d) | (d)-1 | 20 | 39 | 22 | 61 | 35 | 34 | 36 | 34 | 50 |
| | (d)-2 | | | | | | | | | |
| | (d)-3 | | | | | | | | | |
| | (d)-4 | | | | | | | | | |
| Carboxyl-free Polymer (d') | (d')-1 | | | | | | | | | |
| | (d')-2 | | | | | | | | | |
| Acidic Substance (e) other than (b) and (d) | (e)-1 | 1 | 1 | 1 | 1 | 0.3 | 4 | 1 | 1 | 1 |
| | (e)-2 | | | | | | | | | |
| | (e)-3 | | | | | | | | | |
| Total | | 100 | 100 | 100 | 100 | 100 | 100 | 100 | 100 | 100 |
| Test Item | Softening Point (° C.) | 67.0 | 80.0 | 74.0 | 83.0 | 80.0 | 80.0 | 80.0 | 80.0 | poor dispersion stability |
| | Viscosity at 110° C. (mPa·s) | 320 | 1020 | 780 | 1600 | 980 | 980 | 980 | 980 | |
| | Changing Time | very good | very good | very good | very good | Very good | very good | bad | very good | |
| | Moisture Resistance | medium | medium | medium | good | good | good | good | good | |
| | Initial Hue | good | good | good | medium | good | medium | good | bad | |
| | Color Developing Properties | good | good | good | good | medium | good | bad | good | |

| | | Comparative Example No. | | | | | | | | |
|---|---|---|---|---|---|---|---|---|---|---|
| Composition | | 4 | 5 | 6 | 7 | 8 | 9 | 10 | 11 | 12 |
| pH Indicator (a) | (a)-1 | 2 | 2 | 2 | 2 | 2 | 2 | 2 | 2 | 2 |
| | (a)-2 | | | | | | | | | |
| | (a)-3 | | | | | | | | | |
| Surfactant (b) | (b)-1 | 91 | 47 | 21 | 20 | 47 | 45 | 47 | 47 | 47 |
| | (b)-2 | | | | | | | | | |
| | (b)-3 | | | | | | | | | |
| | (b)-4 | | | | | | | | | |
| | (b)-5 | | | | | | | | | |
| Polyalkylene Glycol (c) | (c)-1 | 6 | 0 | 56 | 6 | 15 | 14 | | 15 | 15 |
| | (c)-2 | | | | | | | | | |
| | (c)-3 | | | | | | | | | |
| | (c)-4 | | | | | | | | | |
| Water Soluble Material (c') | (c')-1 | | | | | | | 15 | | |
| Carboxyl-containing Polymer (d) | (d)-1 | 0 | 50 | 20 | 71 | 36 | 33 | 35 | | |
| | (d)-2 | | | | | | | | | |
| | (d)-3 | | | | | | | | | |
| | (d)-4 | | | | | | | | | |
| Carboxyl-free Polymer (d') | (d')-1 | | | | | | | | 35 | |
| | (d')-2 | | | | | | | | | 35 |
| Acidic Substance (e) other than (b) and (d) | (e)-1 | 1 | 1 | 1 | 1 | 0 | 6 | 1 | 1 | 1 |
| | (e)-2 | | | | | | | | | |
| | (e)-3 | | | | | | | | | |
| Total | | 100 | 100 | 100 | 100 | 100 | 100 | 100 | 100 | 100 |
| Test Item | Softening Point (° C.) | 30.0 | 80.0 | 67.0 | 85.0 | 80.0 | 80.0 | poor dispersion stability | | |
| | Viscosity at 110° C. (mPa·s) | 20 | 1050 | 650 | 1850 | 980 | 980 | | | |
| | Changing Time | very good | good | very good | very good | bad | very good | | | |
| | Moisture Resistance | bad | bad | bad | good | good | good | | | |
| | Initial Hue | medium | medium | medium | bad | good | bad | | | |
| | Color Developing Properties | good | good | good | good | bad | good | | | |

Wetness indicator compositions of Examples and Comparative Examples were prepared according to the formulation of Tables 1 and 2.

Examples 1 to 3 illustrate preparation of wet indicator compositions that turn from colorless to different colors by using pH indicators (a) that contain a lactone ring, are substantially colorless at pH 7, and develop a color in an acidic environment.

Examples 4 through 7 illustrate preparation of wetness indicator compositions using various surfactants (b). The color development is somewhat weak with an anionic surfactant. The initial hue is slightly dark with a cationic surfactant. Use of a nonionic surfactant is not associated with such problems. Particularly good results are obtained with a polyoxyethylene alkyl ether.

Examples 8 to 10 illustrate preparation of wetness indicator compositions using various polyalkylene glycols (c).

Examples 11 to 13 illustrate preparation of wetness indicator compositions using various carboxyl-containing polymers (d). Use of an alkylene acrylic acid copolymer provides a composition with particularly excellent performance.

Examples 14 and 15 illustrate preparation of wetness indicator compositions using various acidic substances (e) other than components (b) and (d). Use of an acidic substance that is solid at 23° C. provides a preferred composition with a colorless initial hue.

In Examples 16 and 17 the compounding ratio of the pH indicator (a) that is substantially colorless at pH 7 and develops a color in an acidic environment is varied. When the compounding ratio is out of the range of from 0.5% to 2.5% by weight, the resulting wetness indicator compositions are slightly inferior in initial hue or color developing properties to those having the pH indicator (a) in a ratio within that range but are still useful with no problem.

In Examples 18 and 19 the compounding ratio of the surfactant (b) is varied. When the compounding ratio is out of the range of from 45% to 65% by weight, the resulting wetness indicator compositions are slightly inferior in initial hue or color developing properties to those having the surfactant (b) in a ratio within that range but are still useful with no problem.

In Examples 20 and 21 the compounding ratio of the polyalkylene glycol (c) is varied. When the compounding ratio is out of the range of from 10% to 20% by weight, the resulting wetness indicator compositions are slightly inferior in moisture resistance to those having the polyalkylene glycol (c) in a ratio within that range but are still useful with no problem.

In Example 22 the compounding ratio of the carboxyl-containing polymer (d) is varied. When the compounding ratio is out of the range of from 20% to 60% by weight, the resulting wetness indicator composition is slightly inferior in initial hue to those having the compound (d) in a ratio within that range but still useful with no problem.

In Examples 23 and 24 the compounding ratio of the acidic substance (e) other than components (b) and (d) is varied. When the compounding ratio is out of the range of from 0.5% to 1.5% by weight, the resulting wetness indicator compositions are slightly inferior in initial hue or color developing properties to those having the component (e) in a ratio within that range but still useful with no problem.

Comparative Example 1 does not use a pH indicator (a) substantially colorless at pH 7 and capable of color development in an acidic environment, in which case wetting the composition with ion exchanged water causes no color change. In Comparative Example 2a pH indicator (a) substantially colorless at pH 7 and capable of color development in an acidic environment is used in an amount more than 5% by weight, in which case the initial hue is too dark to provide a sufficient color difference for recognition on color development.

Comparative Example 3 does not use a surfactant (b), in which case the other components are not dispersed even by melting, failing to provide a uniform wetness indicator composition. Wetting with ion exchanged water causes no color development. Comparative Example 4 uses a surfactant (b) in an amount more than 90% by weight. In this case the resulting composition is almost liquid at 23° C. and completely develops a color before 24-hour standing in the moisture resistance test, proving useless.

Comparative Example 5 does not use a polyalkylene glycol (c). In this case, the resulting composition completely develops a color before 24-hour standing in the moisture resistance test, proving unsuited to use. Comparative Example 6 uses the polyalkylene glycol (c) in an amount exceeding 55% by weight. In this case, too, the resulting composition completely develops a color before 24-hour standing in the moisture resistance test, proving unsuited to use.

Comparative Example 7 uses a carboxyl-containing polymer (d) in an amount more than 70% by weight, in which case the initial hue is too dark to provide a sufficient color difference for use.

In Comparative Example 8 an acidic substance (e) other than components (b) and (d) is not compounded, in which case no color development occurs on wetting with ion exchanged water. In Comparative Example 9 the acidic substance (e) other than components (b) and (d) is used in an amount exceeding 5% by weight. In this case, the initial hue is so dark that the color difference on color development is too small for use.

Comparative Example 10 uses a water soluble material (c') in place of the polyalkylene glycol (c). The other components were not dispersed even by melting, failing to provide a uniform wetness indicator composition.

Comparative Examples 11 and 12 use a polymer (d') having no carboxyl group in place of the carboxyl-containing polymer (d). The other components were not dispersed even by melting, failing to provide a uniform wetness indicator composition.

Industrial Applicability

The present invention provides a wetness indicator composition containing a specific pH indicator and a polyalkylene glycol in a specific compounding ratio. The composition has satisfactory thermoplasticity and flexibility, is initially colorless in hue, develops a color in rapid response to being wetted with water to indicate wetness, and has excellent moisture resistance.

While an increase of a hydrophilic polymer, such as a polyalkylene glycol, generally results in reduction in moisture resistance, use of a proper amount of a polyalkylene glycol as in the present invention is rather effective in improving moisture resistance because the pH indicator and the acidic substance are taken in between the polyalkylene glycol and the surfactant.

Having the wetness indicator composition containing components (a) to (e) as a hot melt composition, the absorbent article of the present invention rapidly indicates to a caregiver a discharge of a body fluid, such as urine, feces, or blood. The hot melt composition offers a broad choice of colors to be developed and patterns to be applied so that the absorbent article can be produced with a requested design at a relatively low cost.

The package of absorbent articles according to the present invention contains the absorbent articles of the invention equipped with an indicator (hot melt composition) showing a reversible color change and excellent weatherability. Therefore, the package structure reduces the amount of products that must be disposed of due to undesired color change of the indicator that might have been caused by the humidity before opening the package. Furthermore, the package structure of the invention permits reduction in titanium content to be incorporated into the packaging material to block light that can cause a conventional indicator to change color. As a result, there is provided a high quality package at a lower cost.

The invention claimed is:

1. An absorbent article comprising a topsheet, a backsheet, and an absorbent member between the topsheet and the backsheet and having applied thereon a hot-melt composition that changes color on contact with a body fluid, the hot melt composition comprising (a) 0.1% to 5% by weight of a pH indicator that is substantially colorless at pH 7 and develops a color in an acidic environment, (b) 20% to 90% by weight of a surfactant, (c) 5% to 55% by weight of a polyalkylene glycol, (d) 0% to 70% by weight of a polymer having a carboxyl group, and (e) 0.1% to 5% by weight of an acidic substance other than components (b) and (d):

wherein the hot melt composition undergoes color change on being wetted with a body fluid and then returns to its original color before the color change on being dried.

2. The absorbent article according to claim 1, wherein the hot melt composition changes its color within 1 minute from the contact with a body fluid.

3. A package of an absorbent article comprising the absorbent article according to claim 1 packaged in a packaging material having a titanium content of less than 8% by weight.

4. The absorbent article according to claim 1, wherein the acidic substance other than components (b) and (d) is selected from the group consisting of citric acid, succinic acid, gluconic acid, lactic acid, fumaric acid, malic acid, tartaric acid, acetic acid, formic acid, uric acid, hydrochloric acid, sulfuric acid, phosphoric acid and nitric acid.

* * * * *